United States Patent
Koyama et al.

(10) Patent No.: US 10,450,698 B2
(45) Date of Patent: Oct. 22, 2019

(54) METHOD FOR PRODUCING CELLULOSE-CONTAINING SOLID MATERIAL AND METHOD FOR PRODUCING GLUCOSE

(71) Applicants: IDEMITSU KOSAN CO., LTD., Tokyo (JP); NATIONAL UNIVERSITY CORPORATION HOKKAIDO UNIVERSITY, Sapporo-shi, Hokkaido (JP)

(72) Inventors: Yoshihito Koyama, Ichihara (JP); Takao Masuda, Sapporo (JP); Teruoki Tago, Sapporo (JP)

(73) Assignees: IDEMITSU KOSAN CO., LTD., Tokyo (JP); NATIONAL UNIVERSITY CORPORATION HOKKAIDO UNIVERSITY, Sapporo-Shi, Hokkaido (JP)

( * ) Notice: Subject to any disclaimer, the term of this patent is extended or adjusted under 35 U.S.C. 154(b) by 0 days.

(21) Appl. No.: 15/579,762

(22) PCT Filed: Jun. 10, 2016

(86) PCT No.: PCT/JP2016/067451
§ 371 (c)(1),
(2) Date: Dec. 5, 2017

(87) PCT Pub. No.: WO2016/199924
PCT Pub. Date: Dec. 15, 2016

(65) Prior Publication Data
US 2018/0171552 A1 Jun. 21, 2018

(30) Foreign Application Priority Data
Jun. 11, 2015 (JP) .................................. 2015-118532

(51) Int. Cl.
*D21C 3/20* (2006.01)
*C13B 5/00* (2011.01)
(Continued)

(52) U.S. Cl.
CPC ............... *D21C 3/20* (2013.01); *C12P 19/02* (2013.01); *C12P 19/14* (2013.01); *C13B 5/00* (2013.01);
(Continued)

(58) Field of Classification Search
None
See application file for complete search history.

(56) References Cited

U.S. PATENT DOCUMENTS 3,642,580 A * 2/1972 Ghose ..................... C12P 19/14
435/105
4,713,334 A * 12/1987 Fujishima ............... C12P 19/14
435/162

FOREIGN PATENT DOCUMENTS

JP 2009-531424 9/2009
JP 2011-515082 5/2011
(Continued)

OTHER PUBLICATIONS

Dominguez, et al., "A biorefinery approach based on fractionation with a cheap industrial by-product for getting value from an invasive woody species," Bioresource Technology, (2014), V. 173, pp. 301-308.
(Continued)

*Primary Examiner* — Peter A Salamon
(74) *Attorney, Agent, or Firm* — Foley & Lardner LLP

(57) ABSTRACT

The method for producing a cellulose-containing solid material of the invention includes treating a botanical biomass in a mixed solvent of water and at least one alcohol selected from aliphatic alcohols having 4 to 8 carbon atoms, under
(Continued)

condition A (the concentration of the raw material to be charged into the mixed solvent is 1% by mass or more and 50% by mass or less), condition B (the reaction temperature is 100° C. or higher and 350° C. or lower), and condition C (the reaction time is 0.1 hours or more and 10 hours or less), followed by solid-liquid separation after the treatment to give a cellulose-containing solid material. Accordingly, there are provided a method for producing a cellulose-containing solid material excellent in saccharification performance and a method for producing glucose from the cellulose-containing solid material.

8 Claims, 1 Drawing Sheet

(51) Int. Cl.
   *C13K 1/02* (2006.01)
   *C12P 19/02* (2006.01)
   *D21C 3/00* (2006.01)
   *C12P 19/14* (2006.01)
(52) U.S. Cl.
   CPC ............... *C13K 1/02* (2013.01); *D21C 3/006* (2013.01); *C12P 2201/00* (2013.01)

(56) References Cited

FOREIGN PATENT DOCUMENTS

| JP | 2012-102297 | | 5/2012 |
|---|---|---|---|
| JP | 2012102297 A | * | 5/2012 |
| JP | 2012-210160 | | 11/2012 |
| JP | 2013-541950 | | 11/2013 |
| JP | 5377491 | | 12/2013 |
| JP | 2014-015439 A | | 1/2014 |
| JP | 2015-080759 | | 4/2015 |
| WO | WO-2014/142289 | | 9/2014 |

OTHER PUBLICATIONS

International Search Report Issued in International Patent Application No. PCT/JP2016/067451 dated Sep. 6, 2016.
Japanese Office Action dated Jan. 8, 2019 in corresponding application No. 2015-118532.
Japanese Patent Office, "Notification of Reasons for Refusal," issued in connection with Japanese Patent Application No. 2015-118532, dated Jan. 8, 2019.
JP Office Action issued in the corresponding Japanese Patent Application Ser. No. 2015-118532, dated Jun. 18, 2019.

* cited by examiner

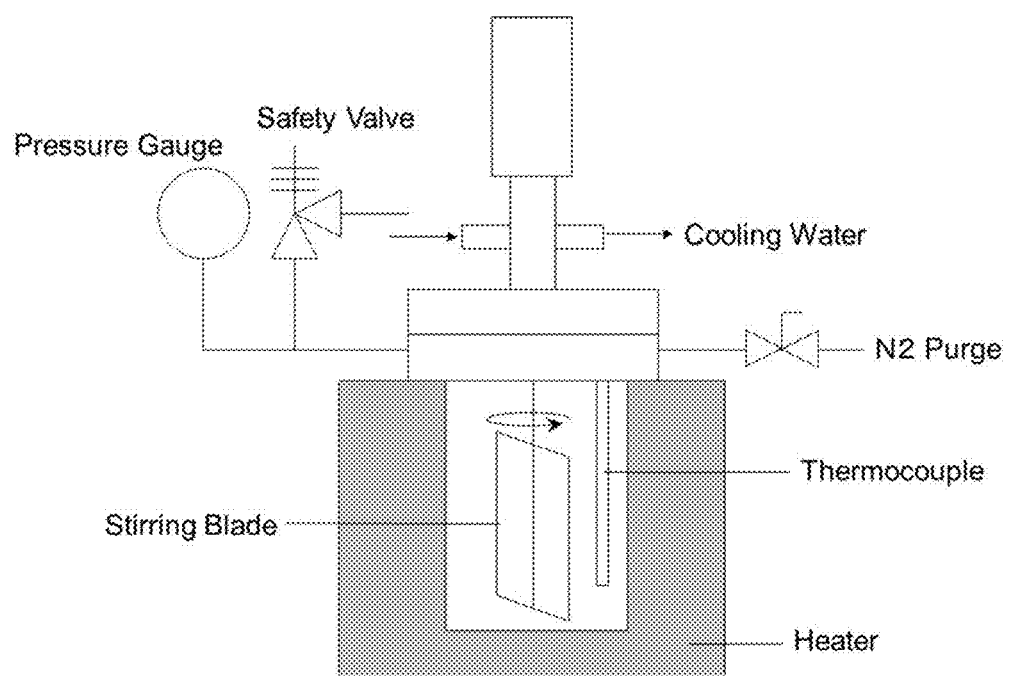

METHOD FOR PRODUCING CELLULOSE-CONTAINING SOLID MATERIAL AND METHOD FOR PRODUCING GLUCOSE

RELATED APPLICATIONS

The present application claims priority under 35 USC 371 to International Patent Application number PCT/JP2016/067451, filed Jun. 10, 2016, which claims priority to Japanese Patent Application No. 2015-118532, filed Jun. 11, 2015. The contents of these applications are hereby incorporated by reference in their entireties.

TECHNICAL FIELD

The present invention relates to a method for producing a cellulose-containing solid material and a method for producing glucose, using a biomass as a raw material.

BACKGROUND ART

Due to a recent increase in environmental consciousness, a raw material derived from a biomass has been desired. However, for example, as is especially noticeable in the production of bioethanol, as the raw material derived from a biomass, a raw material such as starch or sugar that competes with foods is used in many cases and accordingly, there has been pointed out such problems that the use leads to an increase in food prices and a decrease in food production or the like. Therefore, attention has been currently attracted to a technique for producing biofuels, biochemicals and others from a cellulosic biomass that does not compete with foods.

Examples of the cellulosic biomass that does not compete with foods include trunks and empty fruit bunches of palm, fibers and seeds of palm fruits, bagasse (strained lees of sugar cane (including high biomass content sugar cane)), rice straws, wheat straws, cobs, stems and leaves of corn, corn residues (corn stovers, corn cobs, corn hulls), sorghum (including sweet sorghum) residues, Jatropha seed coats and hulls, cashew hulls, wood chips, switchgrass, Erianthus, energy crops, etc.

One example of using a cellulosic biomass not competing with foods as a raw material is sugar production by enzymatic saccharification treatment. However, all the above-mentioned cellulosic biomasses contain lignin in addition to cellulose and hemicellulose that can be converted into sugar. Lignin has a complicated three-dimensional structure, and therefore impedes approach to cellulose by a cellulolytic enzyme in enzymatic saccharification treatment. Consequently, presence of a large amount of lignin in a cellulosic biomass provides a problem that the efficiency of enzymatic reaction could be hardly better.

Given the situation, as one method for sufficiently carrying out enzymatic saccharification treatment, a method of carrying out enzymatic hydrolysis after pretreatment of a cellulosic biomass with aqueous ammonia has been proposed (see PTL 1). In addition, a method of carrying out enzymatic hydrolysis after pretreatment of a cellulosic biomass by vapor explosion has also been proposed (see PTL 2).

However, both the above-mentioned methods are still problematic in point of the yield of glucose to be obtained, and further improvement is desired.

CITATION LIST

Patent Literature

PTL 1: JP 5377491 B2
PTL 2: JP 2013-541950 A

SUMMARY OF INVENTION

Technical Problem

Accordingly, an object of the present invention is to provide a method for producing a cellulose-containing solid material excellent in saccharification performance, and to provide a method for producing glucose from the cellulose-containing solid material.

Solution to Problem

The present inventors have found that the above-mentioned problems can be solved by treating a botanical biomass under specific conditions.

Specifically, the gist of the present invention includes the following:

[1] A method for producing a cellulose-containing solid material, including:
treating a botanical biomass in a mixed solvent of water and at least one alcohol selected from aliphatic alcohols having 4 to 8 carbon atoms, under the following conditions:
Condition A: the concentration of the raw material to be charged into the mixed solvent is 1% by mass or more and 50% by mass or less,
Condition B: the reaction temperature is 100° C. or higher and 350° C. or lower, and
Condition C: the reaction time is 0.1 hours or more and 10 hours or less, followed by solid-liquid separation after the treatment to give a cellulose-containing solid material.
[2] The method for producing a cellulose-containing solid material according to [1], wherein the molar ratio of water to the alcohol (water/alcohol) in the mixed solvent is from 1/1 to 40/1.
[3] The method for producing a cellulose-containing solid material according to [1] or [2], wherein the aliphatic alcohol is at least one selected from 1-butanol, 2-butanol and 2-methyl-1-propanol.
[4] The method for producing a cellulose-containing solid material according to any of [1] to [3], wherein the botanical biomass is a herbaceous biomass.
[5] A method for producing glucose, including subjecting the cellulose-containing solid material obtained according to the production method of any one of [1] to [4] to enzymatic saccharification treatment.

Advantageous Effects of Invention

According to the present invention, there can be provided a method for producing a cellulose-containing solid material excellent in saccharification performance, and a method for producing glucose from the cellulose-containing solid material.

BRIEF DESCRIPTION OF DRAWING

FIG. 1 is a view showing a batch-type reaction apparatus used in Examples.

DESCRIPTION OF EMBODIMENTS

A method for producing a cellulose-containing solid material of an aspect of the present invention is described in detail hereinunder.

[Method for Producing Cellulose-Containing Solid Material]

The method for producing a cellulose-containing solid material in this aspect includes treating a botanical biomass in a mixed solvent of water and at least one alcohol selected from aliphatic alcohols having 4 to 8 carbon atoms under the following conditions, followed by solid-liquid separation after the treatment to give a cellulose-containing solid material.

The conditions are as follows:

Condition A: the concentration of the raw material to be charged into the mixed solvent is 1% by mass or more and 50% by mass or less, Condition B: the reaction temperature is 100° C. or higher and 350° C. or lower, and Condition C: the reaction time is 0.1 hours or more and 10 hours or less.

Here, the concentration of the raw material to be charged means a ratio by mass of the raw material put into the mixed solvent to the mixed solvent, and contains any raw material component insoluble in the mixed solvent.

<Step of Separating Solid Fraction Containing Cellulose-Containing Solid Material>

The step of separating a solid fraction containing a cellulose-containing solid material includes treating a botanical biomass in a mixed solvent of water and at least one alcohol selected from aliphatic alcohols having 4 to 8 carbon atoms under the above-mentioned conditions, followed by solid-liquid separation after the treatment.

(Raw Material)

The botanical biomass includes a woody biomass and a herbaceous biomass. The woody biomass includes coniferous trees and broad-leaf trees such as cedar trees, cypress trees, false cypress trees, cherry trees, eucalyptus trees, beech trees, bamboos, etc. The herbaceous biomass includes trunks and empty fruit bunches of palm, fibers and seeds of palm fruits, bagasse (sugar cane and strained lees of sugar cane having a high biomass content), cane tops (tops and leaves of sugar cane), rice straws, wheat straws, corn cobs, stovers and residues (corn stovers, corn cobs, corn hulls), sorghum (including sweet sorghum) residues, Jatropha seed coats and hulls, cashew shells, switchgrass, Erianthus and energy crops, etc.

Of those, from the viewpoint of the availability and the compatibility with the production method to be employed in the present invention, a herbaceous biomass is preferred. Empty fruit bunches of palm, wheat straws, corn stovers and residues, bagasse and cane tops are more preferred, and bagasse and cane tops are even more preferred. As the botanical biomass, ground materials may be used. In addition, the biomass may be in any form of blocks, chips or powders.

From the raw material, a cellulose-containing solid material is obtained according to the following treatment.

(Solvent for Use for Separation of Solid Fraction)

The solvent for use for separation of a solid fraction containing a cellulose-containing solid material is described. The alcohol for use for the solvent is an aliphatic alcohol having 4 to 8 carbon atoms, and undergoes two-phase separation from water at 0° C. or higher and 50° C. or lower.

For example, the alcohol may be a saturated linear alcohol such as 1-butanol, 1-pentanol, 1-hexanol, 1-heptanol, 1-octanol or the like, as well as an unsaturated linear alcohol. The alcohol may also be an alcohol of a branched aliphatic hydrocarbon. It may also be an unsaturated branched alcohol.

Here, two-phase separation means a state where almost all the mixed solvent has separated in two phases, but includes a state where the aqueous phase and the alcohol phase have dissolved together though slightly. The treatment of removing alcohol from the alcohol phase includes a treatment of removing the aqueous phase slightly dissolving in the alcohol phase.

Among these alcohols, from the viewpoint of two-phase separation from water at 0° C. or higher and 50° C. or lower, at least one selected from 1-butanol, 2-butanol, 2-methyl-1-propanol, 1-pentanol and 1-hexanol is preferred, and 1-butanol, 2-butanol and 2-methyl-1-propanol are more preferred.

The molar ratio of water to alcohol (water/alcohol) is preferably 1/1 to 40/1, more preferably 1.5/1 to 30/1, even more preferably 2/1 to 24/1. When the ratio of water to alcohol oversteps the above-mentioned range, water and alcohol could not undergo two-phase separation under predetermined conditions, as the case may be. In addition, in a mixing ratio not falling within the above-mentioned range, lignin separation and removal may be insufficient, as the case may be.

An alcohol capable of undergoing two-phase separation from water is preferred as facilitating alcohol recovery. As opposed to this, a mixed solvent with an alcohol which does not undergo two-phase separation at 0° C. or higher and 50° C. or lower and which has a boiling point lower than that of water is unsuitable as a solvent from the viewpoint of energy loss in solvent separation.

In this aspect, examples of water to be used as the solvent include tap water, industrial-use water, ion-exchanged water, distilled water, etc.

(Conditions in the Step of Separating Solid Fraction that Contains Cellulose-Containing Solid Material, from Raw Material)

The concentration of the raw material to be charged into the solvent of the condition A is 1% by mass or more and 50% by mass or less, preferably 3% by mass or more and 20% by mass or less, more preferably 5% by mass or more and 15% by mass or less. When the raw material concentration is less than 1% by mass, much energy is needed for solvent heating and for solvent removal so that the energy efficiency in the production process worsens. When the material is more than 50% by mass, the solvent amount is not sufficient and lignin separation efficiency lowers.

The reaction temperature of the condition B is 100° C. or higher and 350° C. or lower, preferably 150° C. or higher and 300° C. or lower, more preferably 170° C. or higher and 270° C. or lower. When the temperature is lower than 100° C., lignin separation could hardly occur, but when higher than 350° C., cellulose may decompose and lignin may again polymerize to form coke unfavorably.

The reaction time of the condition C is 0.1 hours or more and 10 hours or less, preferably 0.2 hours or more and 8 hours or less, even more preferably 1 hour or more and 6 hours or less, still more preferably 1 hour or more and 3 hours or less. When the time is less than 0.1 hours, separation could hardly go on, but when more than 10 hours, cellulose may decompose and lignin may again polymerize so that the amount of coke to be formed could not be suppressed.

In the separation step, the cellulose-containing solid material that is a solid fraction in the alcohol phase and the aqueous phase is separated.

According to the separation method for the cellulose-containing solid material in this aspect, the cellulose-containing solid material contained in the botanical biomass can be recovered efficiently and at a high purity as the solid fraction to be formed in the form of a deposit in the alcohol phase and the aqueous phase.

According to the separation method for the cellulose-containing solid material in this aspect, lignin contained in the raw material dissolves in the alcohol phase of the solvent. Consequently, the amount of lignin contained in cellulose, hemicellulose and their degradation products can be reduced.

(Other Conditions)

Apart from the above-mentioned conditions A to C, it is desirable that the pressure of the reaction system in the separation step is set to be 0.5 MPa or more and 30 MPa or less. A more preferred condition may be adequately settled, as influenced by the amount of water and alcohol and by temperature. The separation step may be carried out in air. Preferably, the separation step is carried out in an atmosphere where oxygen has been reduced by nitrogen purging, for preventing polymerization by oxidation.

<Step of Washing Solid Fraction with Water>

The production method for a cellulose-containing solid material in this aspect may include a step of washing the solid fraction obtained through solid-liquid separation, with water. In the water-washing step, water is used in an amount of 100 parts by mass or more and 10,000 parts by mass or less relative to 100 parts by mass of the resultant solid fraction, and after stirring, the solid fraction is separated from a liquid phase through filtration. The amount of water to be used in the water-washing step is preferably 1,000 parts by mass or more and 5,000 parts by mass or less, more preferably 1,000 parts by mass or more and 2,000 parts by mass or less. When the amount is less than 100 parts by mass, a sufficient washing effect could not be attained, but when more than 10,000 parts by mass, the equipment may be too large.

In the water-washing step, the mixed solvent is removed and components soluble in water such as hemicellulose and the like are removed by dissolution. Preferably, the water-washing step is carried out plural times, more preferably carried out repeatedly three times or more. After the water-washing step, a cellulose-containing solid material is obtained.

According to the production method for a cellulose-containing solid material in this aspect, the cellulose-containing solid material in a biomass can be recovered as a solid fraction to remain as a residue in an aqueous phase.

In addition, according to the separation method for a cellulose-containing solid material in this aspect, lignin contained in a raw material can be dissolved out and separated in the alcohol phase of the above-mentioned solvent, and the amount of lignin contained in cellulose, hemicellulose and degradation products thereof can be thereby reduced.

Though not specifically limited, the separation mode in the production method in this aspect of the present invention may be static separation. For example, an ordinary batch-type reactor, a semibatch-type reactor or the like may be used. In addition, a system where a slurry containing a botanical biomass, water and an alcohol is processed for separation with extrusion thereof via a screw, a pump or the like may be employed.

<Characteristics of Resultant Cellulose-Containing Solid Material>

The cellulose-containing solid material extracted according to the above-mentioned method contains cellulose and a cellulose degradation product obtained through degradation of cellulose in an amount of 60% by mass or more and 90% by mass or less as a solid content, lignin in an amount of 5% by mass or more and 30% by mass or less, and hemicellulose and a hemicellulose degradation product obtained by degradation of hemicellulose in an amount of 0% by mass or more and 5% by mass or less, based on the total amount of the cellulose-containing solid material.

When the amount of cellulose and a cellulose degradation product obtained through degradation of cellulose is less than 60% by mass, or when the amount of lignin is more than 30% by mass, the saccharification rate in obtaining glucose through enzymatic saccharification treatment may lower.

When the amount of hemicellulose and a hemicellulose degradation product obtained through degradation of hemicellulose is more than 5% by mass, separation and removal of lignin bonding to hemicellulose may be insufficient and the saccharification rate in obtaining glucose through enzymatic saccharification treatment may lower.

From the above-mentioned viewpoints, the amount of cellulose and a cellulose degradation product obtained through degradation of cellulose contained in the cellulose-containing solid material is preferably 70% by mass or more and 90% by mass or less, more preferably 75% by mass or more and 90% by mass or less based on the total amount of the cellulose-containing solid material.

The amount of lignin contained in the cellulose-containing solid material is preferably 5% by mass or more and 25% by mass or less, more preferably 5% by mass or more and 20% by mass or less based on the total amount of the cellulose-containing solid material.

Further, the amount of hemicellulose and a hemicellulose degradation product obtained through degradation of hemicellulose contained in the cellulose-containing solid material is preferably 0% by mass or more and 3% by mass or less, more preferably 0% by mass or more and 2% by mass or less based on the total amount of the cellulose-containing solid material.

<Use of Cellulose-Containing Solid Material>

Cellulose contained in the cellulose-containing solid material obtained according to the production method for a cellulose-containing solid material of the present invention has a small lignin content and is therefore favorably used in saccharification treatment with acid and enzyme.

The cellulose-containing solid material obtained according to the production method in this aspect is, as compared with a cellulose-containing solid material obtained by any other method, in a readily-openable state. Therefore its advantage is that its use evolvement is easy.

According to a known method, ethanol and butanol can be obtained from the cellulose-containing solid material obtained according to the production method in this aspect.

In addition, from the cellulose-containing solid material obtained according to the production method in this aspect, rubber and tire reinforcing materials as alternatives to resin reinforcing fibers and chemical fibers, such as cellulose nanofibers and the like, food additives such as carboxymethyl cellulose, oligosaccharides and the like, and chemical products such as lactic acid, succinic acid and the like can be obtained.

<Use of Hemicellulose and Lignin Separated in the Production Method>

From hemicellulose separated according to the production method for a cellulose-containing solid material in this aspect, food additives such as oligosaccharides, xylitol and the like, and chemical products such as furfural and the like can be obtained usefully.

Specifically, lignin separated in the production method for a cellulose-containing solid material in this aspect can be used as fuel, and a water repellent material for cement. Apart from these, lignin is also applicable to base resin raw materials for phenol resins, epoxy resins and polyurethane resins, additives (curing agents) to epoxy resins, modifiers (flame retardants) for polyurethane resins, etc. These are owing to the characteristic of lignin having a phenolic structural unit.

Here, for use as a base resin raw material, any known conventional method is employable. As one example, there is mentioned a resin composition containing lignin and a known crosslinking agent typified by hexamethylenetetramine.

Various filler and industrially-available ordinary phenolic resins may be added, as needed, to the resin composition containing lignin and a crosslinking agent. Such a resin composition can be used as heat-insulating materials for residential use, electronic parts, resins for frac sand, resins for coated sand, resins for impregnation, resins for lamination, resins for FRP moldings, automobile parts, reinforcing materials for car tires, etc.

In addition, by introduction of an epoxy resin into lignin and by use of lignin as an epoxy resin curing agent, application of lignin to epoxy resins becomes possible. Furthermore, by introducing a vinyl group, a maleimide group, an isocyanate group or the like into lignin according to a known method, application of lignin to industrial resins in a broad range becomes possible.

[Production Method for Glucose]

Using the cellulose-containing solid material obtained according to the production method for a cellulose-containing solid material in this aspect of the present invention, glucose may be produced. Specifically, the production method for glucose in this aspect of the present invention includes treating a botanical biomass in a mixed solvent of water and at least one alcohol selected from aliphatic alcohols having 4 to 8 carbon atoms, under the following conditions, followed by solid-liquid separation after the treatment to give a cellulose-containing solid material, and subjecting the cellulose-containing solid material enzymatic saccharification treatment, thereby obtaining glucose. The conditions for the treatment for obtaining the cellulose-containing solid material are as follows.

Condition A: the concentration of the raw material to be charged into the mixed solvent is 1% by mass or more and 50% by mass or less, Condition B: the reaction temperature is 100° C. or higher and 350° C. or lower, and Condition C: the reaction time is 0.1 hours or more and 10 hours or less.

Here, the concentration of the raw material to be charged means a ratio by mass of the raw material put into the mixed solvent to the mixed solvent, and contains any raw material component insoluble in the mixed solvent.

In the production method for glucose in this aspect, the conditions for the enzymatic saccharification treatment are as follows.

An enzyme capable of acting on cellulose and a cellulose degradation product formed through degradation of cellulose to be contained in a cellulose-containing solid material may be added to the material in an amount of 0.1% by mass or more and 200% by mass or less relative to the total amount of the cellulose-containing solid material. The enzymatic activity for the enzymatic saccharification treatment may be 100 U/g or more and 10,000 U/g or less. The treatment temperature in the enzymatic saccharification treatment may be 30° C. or higher and 70° C. or lower, at which the enzyme can be activated and the saccharification rate can be thereby increased. The treatment time for the enzymatic saccharification treatment may be 12 hours or more and 168 hours or less, in which the enzyme can be activated and the saccharification rate can be thereby increased.

EXAMPLES

Hereinunder, the present invention is described in more detail with reference to Examples. The present invention is not restricted to the following Examples.

Production of Cellulose-Containing Solid Material

Production Example 1

Bagasse was selected as a botanical biomass, and a sample thereof having a sample size of 5 mm square or less was prepared. The sample and a mixed solvent of water/1-butanol in a ratio of 8/1 were put into a SUS (stainless) batch-type device having an inner volume of 0.92 L (FIG. 1). The total amount of the solvent was 315 g. Regarding the concentration of the raw material to be charged, raw material/solvent=1/10.

The SUS batch-type device was purged with nitrogen, then heated up to 200° C., and the contents were treated for 2 hours. At this time, the inner pressure (vapor pressure of water and 1-butanol) was 1.9 MPa. The treatment time was the lapse time after the device reached 200° C. For temperature measurement, a thermocouple was used.

After the treatment, the SUS batch-type device was cooled, and after the temperature lowered to around room temperature, the solid fraction and the liquid phase were separated from each other through filtration.

200 g of water was added to the solid fraction, stirred for 30 minutes, and the solid fraction and the liquid phase were separated through filtration. The operation was repeated three times to give a cellulose-containing solid material A.

Production Examples 2 to 6

The raw material biomass shown in Table 1 was treated using the same mixture solution as in Production Example 1 and under the same conditions as in Production Example 1 to separate the solid fraction and the liquid phase through filtration. Further, according to the same operation as in Production Example 1, cellulose-containing solid materials B to F were obtained. The results of composition analysis of the resultant cellulose-containing solid materials are shown in Table 1.

Comparative Production Example

As a raw material, bagasse (sample size 10 cm×2 cm square or less) was put into a 2-L pressure container of a vapor explosion apparatus, then vapor pressure was introduced thereinto under pressure, and kept at 210° C. for 5 minutes. Subsequently, the valve was rapidly opened to produce a cellulose-containing solid material A'.

<Composition Analysis of Cellulose-Containing Solid Material>

The component composition in Table 1 was calculated according to constituent sugar analysis after the following pretreatment.

(Pretreatment)

As pretreatment, the raw material to be a sample was ground using a Wiley mill, and dried at 105° C.

(Analysis of Constituent Sugar)

An appropriate amount of the sample of a cellulose-containing solid material was metered, 72% sulfuric acid was added, and left at 30° C. for 1 hour with stirring as needed. While mixed and diluted with pure water, the reaction liquid was completely transferred into a pressure bottle and treated at 120° C. in an autoclave for 1 hour, and subsequently filtered into a filtrate and a residue. The monosaccharide in the filtrate was quantified through high-performance liquid chromatography. C6 polysaccharide (mainly glucan) was defined as cellulose, and C5 polysaccharide (mainly xylan) was as hemicellulose.

(Lignin)

The residue obtained through filtration in the process of constituent sugar analysis was dried at 105° C., and the weight thereof was measured to calculate the degradation residue ratio. By ash correction, the lignin content was calculated.

centrifuge tube to make about 20 mL and pH 5, and subsequently an enzyme (Cell Lyzer ACE, manufactured by Nagase ChemteX Corporation) was put thereinto in an enzymatic amount shown in Table 2. The centrifuge tube was shaken in a thermostat bath at 50° C. at 120 rpm for 72 hours.

When 1 ml of an enzyme is added to 4 ml of a 0.625% solution (pH 4.5) of 0.625% sodium carboxymethyl cellulose, and made to act thereon at 40° C. for 30 minutes, the enzymatic activity to generate a reduction power corresponding to 1 μmol of glucose for 1 minute is expressed as 1 CUN. The above-mentioned enzyme has an enzymatic activity of 1,600 CUN/g or more.

<Analysis of Sugar Obtained in Enzymatic Sacchrification>

Sugar (glucose) was analyzed through HPLC.

(Measurement Conditions)

Column: Shodex SP-G (guard column)+SP0810, manufactured by Showa Denko K.K.

Mobile phase: distilled water (HPLC grade)

Detector: RI (inside cell, 60° C.)

Column temperature: 80° C.

Injection amount: 50 μL

Standard sample for calibration curve: D-(+)-glucose, D-(+)-xylose, manufactured by Tokyo Chemical Industry Co., Ltd.

(Sample Preparation)

Using a pipetter, 0.2 mL of the sample solution was taken in a 10-mL vial bottle, and 1.8 mL of distilled water was

TABLE 1

|  | Production Example 1 | Production Example 2 | Production Example 3 | Production Example 4 | Production Example 5 | Production Example 6 | Comparative Production Example |
|---|---|---|---|---|---|---|---|
| Botanical Biomass | bagasse 1 | bagasse 2 | bagasse 3 | bagasse 4 | Japanese cedar | bamboo | bagasse 1 |
| Cellulose-Containing Solid Material | A | B | C | D | E | F | A' |
| Production Area | Thailand | Thailand | Vietnam | Brazil | Japan | Japan | Thailand |
| Cellulose (mass %) | 62 | 76 | 70 | 78 | 70 | 90 | 55 |
| Lignin (mass %) | 21 | 14 | 10 | 8 | 25 | 7 | 32 |
| Hemicellulose (mass %) | 2 | 1 | 1 | 1 | 1 | 1 | 4 |
| Other Components (mass %) | 15 | 9 | 19 | 13 | 4 | 2 | 9 |

Production of Glucose by Enzymatic Saccharification Treatment

Examples 1 to 6 and Comparative Example

One g (dry weight) of each of the cellulose-containing solid materials A to F obtained in Examples 1 to 6 or the cellulose-containing solid material A' obtained in Comparative Production Example was put into a 50-mL centrifuge tube, and sterilized at 121° C. for 20 minutes. An acetate buffer sterilized in the same manner was added to the added thereto and fully mixed. Specifically, a 1/10 dilution solution was prepared. This was taken in a vial bottle.

(Metering Method)

Using a calibration curve, the glucose concentration (g-glucose/L) was calculated. The saccharification rate (%) is calculated on the basis of the following expression.

Saccharification Rate (%)=(amount of glucose in enzymatic saccharification liquid (g))/(amount of glucose in cellulose-containing solid material (g))×100

TABLE 2

| | Saccharification Rate (%) | | | | | | |
|---|---|---|---|---|---|---|---|
| Amount of Enzyme (mL) | Example 1 | Example 2 | Example 3 | Example 4 | Example 5 | Example 6 | Comparative Example |
| 0.025 | 33 | 38 | 45 | 43 | 30 | 32 | 29 |
| 0.05 | 55 | 63 | 70 | 67 | 47 | 51 | 43 |
| 0.1 | 76 | 82 | 89 | 87 | 63 | 70 | 54 |
| 0.15 | 88 | 91 | 97 | 96 | 76 | 83 | 61 |
| 0.2 | 97 | 99 | 100 | 100 | 85 | 90 | 67 |

[Evaluation Results]

Irrespective of the raw material species, the samples of Examples using the cellulose-containing solid materials A to F obtained in Production Examples 1 to 6 of the production method of the present invention contained a smaller content of lignin that interferes with approach of cellulase, as compared with the sample of Comparative Example using the cellulose-containing solid material A' obtained in Comparative Production Example including pretreatment by vapor explosion. Accordingly, it is presumed that the saccharification rate in the enzymatic saccharification treatment could be increased.

Consequently, using the cellulose-containing solid material obtained according to the production method of the present invention, the saccharification rate in enzymatic saccharification treatment can be improved without interfering with approach of cellulase.

The invention claimed is:

1. A method for producing a cellulose-containing solid material, comprising:
    treating a botanical biomass in a mixed solvent of water and at least one alcohol selected from aliphatic alcohols having 4 to 8 carbon atoms, under the following conditions:
    Condition A: a concentration of the botanical biomass charged into the mixed solvent is 1% by mass or more and 50% by mass or less,
    Condition B: a reaction temperature is 100° C. or higher and 350° C. or lower, and
    Condition C: a reaction time is 0.1 hours or more and 10 hours or less,
    followed by performing a solid-liquid separation after the treatment to give a solid fraction, and
    washing the solid fraction with water to obtain the cellulose-containing solid material.

2. The method for producing a cellulose-containing solid material according to claim 1, wherein the molar ratio of water to the alcohol (water/alcohol) in the mixed solvent is from 1/1 to 40/1.

3. The method for producing a cellulose-containing solid material according to claim 1, wherein the aliphatic alcohol is at least one selected from 1-butanol, 2-butanol and 2-methyl-1-propanol.

4. The method for producing a cellulose-containing solid material according to claim 1, wherein the botanical biomass is a herbaceous biomass.

5. A method for producing glucose, comprising subjecting the cellulose-containing solid material obtained according to the production method of claim 1 to enzymatic saccharification treatment.

6. The method for producing a cellulose-containing solid material according to claim 1, wherein an amount of the water used washing the solid fraction is 100 parts by mass or more and 10,000 parts by mass or less relative to 100 parts by mass of the resultant solid fraction.

7. The method for producing a cellulose-containing solid material according to claim 1, wherein the cellulose-containing solid material contains cellulose and a cellulose degradation product in an amount of 60% by mass or more and 90% by mass or less as a solid content, lignin in an amount of 5% by mass or more and 30% by mass or less, and hemicellulose and a hemicellulose degradation product in an amount of 0% by mass or more and 5% by mass or less, based on the total amount of the cellulose-containing solid material.

8. The method for producing a cellulose-containing solid material according to claim 1, wherein the botanical biomass is treated without a solid acid catalyst.

* * * * *